US00PP37323P2

(12) United States Plant Patent
van Dijk

(10) Patent No.: US PP37,323 P2
(45) Date of Patent: Mar. 10, 2026

(54) ***ANTHURIUM* PLANT NAMED 'AN2297549'**

(50) Latin Name: *Anthurium andreanum*
Varietal Denomination: AN2297549

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/315,584

(22) Filed: Aug. 31, 2025

(51) Int. Cl.
*A01H 6/00* (2018.01)
*A01H 5/02* (2018.01)

(52) U.S. Cl.
USPC ..... Plt./365
CPC ..... *A01H 6/00* (2018.05)

(58) Field of Classification Search
USPC ..... Plt./365
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Anthurium* plant named 'AN2297549', characterized by its upright to outwardly arching plant habit; freely clumping growth habit; bushy and dense plants; narrowly deltoid-shaped dark green-colored leaves; freely flowering habit; open inflorescences that are positioned above the foliar plane on strong scapes; cordate-shaped spathes that are green, yellow green and red in color; and reddish orange to dark purplish red-colored spadices.

2 Drawing Sheets

Figure 1:
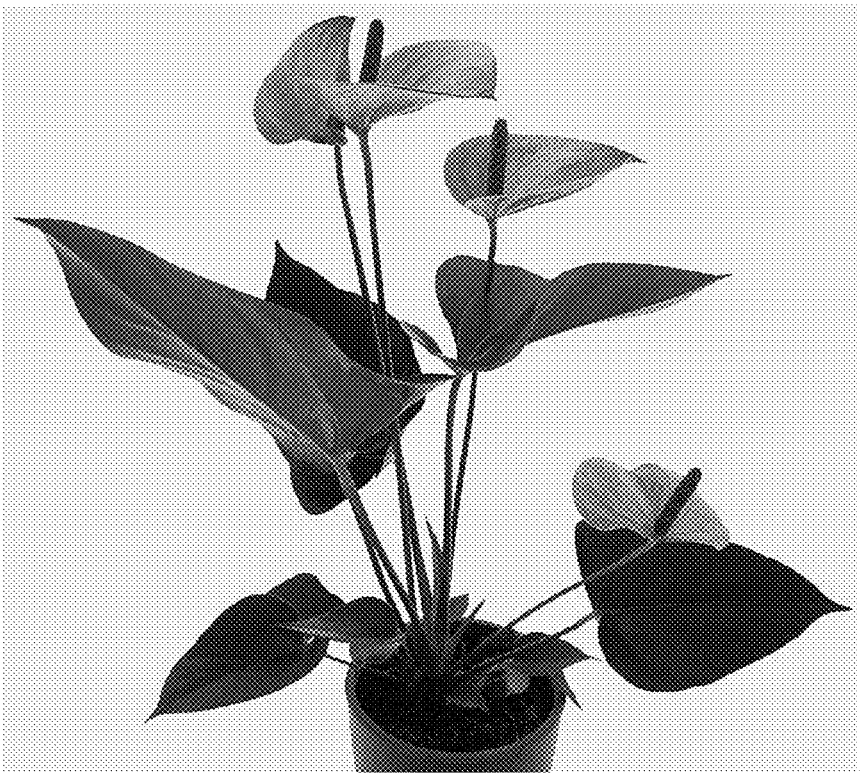

Botanical designation: *Anthurium andreanum.*
Cultivar denomination: 'AN2297549'.

CROSS-REFERENCED TO CLOSELY-RELATED APPLICATION

A European Community Plant Breeder's Rights application for the instant plant was filed by the Applicant/Assignee of the instant application, Anthura B.V. of Bleiswijk, The Netherlands on Nov. 20, 2024, application number 2024/2699. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2297549'.

The new *Anthurium* plant is a product of a controlled breeding program conducted by the Inventor in Bleiswijk, The Netherlands. The objective of the breeding program is to create new *Anthurium* plants with durable multi-colored spathes.

The new *Anthurium* plant originated from a cross-pollination made by the Inventor in October, 2015 in Bleiswijk, The Netherlands of a proprietary breeding selection of *Anthurium andreanum* identified as code number 13-031237-0002, not patented, as the female, or seed, parent with a proprietary breeding selection of *Anthurium andreanum* identified as code number 13-034100-0002, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in October, 2017.

Asexual reproduction of the new *Anthurium* plant by in vitro meristem propagation in a controlled environment in Bleiswijk, The Netherlands since October, 2017 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2297549'. These characteristics in combination distinguish 'AN2297549' as a new and distinct *Anthurium* plant:

1. Upright to outwardly arching plant habit.
2. Freely clumping growth habit; bushy and dense plants.
3. Narrowly deltoid-shaped dark green-colored leaves.
4. Freely flowering habit.
5. Open inflorescences that are positioned above the foliar plane on strong scapes.
6. Cordate-shaped spathes that are green, yellow green and red in color.
7. Reddish orange to dark purplish red-colored spadices.

Plants of the new *Anthurium* differ primarily from plants of the female parent selection in the following characteristics:

1. Spathes of plants of the new *Anthurium* are larger than spathes of plants of the female parent selection.
2. Spadices of plants of the new *Anthurium* are moderately concave whereas spadices of plants of the female parent selection are concave to convex.

Plants of the new *Anthurium* differ primarily from plants of the male parent selection in the following characteristics:

1. Spathes of plants of the new *Anthurium* are green, yellow green and red in color whereas spathes of plants of the male parent selection are creamy white in color.
2. Fully developed spadices of plants of the new *Anthurium* are dark purplish red in color whereas fully developed spadices of plants of the male parent selection are pink in color.

Plants of the new *Anthurium* can also be compared to plants of *Anthurium andreanum* 'AN2112420', disclosed in U.S. Plant Pat. No. 35,162. In side-by-side comparisons, plants of the new *Anthurium* differ primarily from plants of 'AN2112420' in the following characteristics:

1. Spathes of plants of the new *Anthurium* are larger than spathes of plants of 'AN2112420'.
2. Spathes of plants of the new *Anthurium* are green, yellow green and red in color whereas spathes of plants of 'AN2112420' are pink, red and green in color.
3. Fully developed spadices of plants of the new *Anthurium* are dark purplish red in color whereas fully developed spadices of plants of 'AN2112420' are red purple in color.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2297549' grown in a container.

Figure 2:
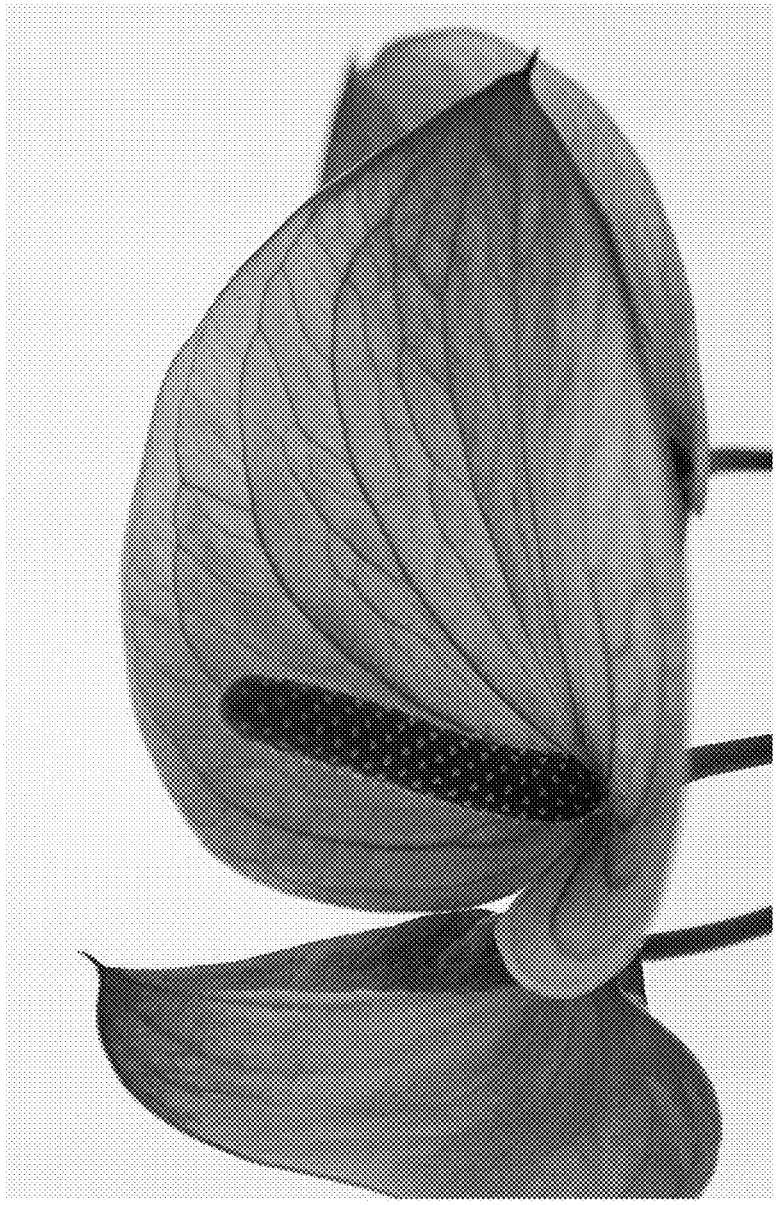

The photograph on the second sheet (FIG. 2) is a close-up view of typical inflorescences of 'AN2297549'.

DETAILED BOTANICAL DESCRIPTION

The aforementioned photographs and following observations and measurements describe plants grown in 14-cm containers during the winter in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were eleven months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2297549'.

Parentage:

*Female, or seed, parent*.—Proprietary breeding selection of *Anthurium andreanum* identified as code number 13-031237-0002, not patented.

*Male, or pollen, parent*.—Proprietary breeding selection of *Anthurium andreanum* identified as code number 13-034100-0002, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically creamy white in color; actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading plant habit; overall shape, broadly elliptic.

*Growth habit*.—Freely clumping habit imparting a bushy and dense appearance; in a single year of production, about 40 individual plants can be harvested per plant; moderately vigorous growth habit and moderate growth rate.

*Plant height, from soil level to top of leaf plane*.—About 32.5 cm.

*Plant height, from soil level to top of inflorescences*.—About 47.4 cm.

*Plant diameter or spread*.—About 47.2 cm.

Leaf description:

*Arrangement*.—Alternate; simple.

*Length*.—About 21.5 cm.

*Width*.—About 15 cm.

*Shape*.—Narrowly deltoid.

*Apex*.—Apiculate with a mucronate tip.

*Base*.—Cordate to hastate.

*Margin*.—Entire; coarsely undulate.

*Texture, upper and lower surfaces*.—Smooth, glabrous; moderately coriaceous.

*Venation pattern*.—Pinnate.

*Color*.—Developing leaves, upper surface: Close to 146A; narrow marginal edges, close to 144A. Developing leaves, lower surface: Close to 146B; narrow marginal edges, close to 144A. Fully expanded leaves, upper surface: Close to a blend of 147A and N189A; narrow marginal edges, close to 146A; toward the apex and mucronate apex, close to 164A; venation, close to a blend of 143B and 144A. Fully expanded leaves, lower surface: Close to 146A; towards the apex and mucronate apex, close to 199A; venation, close to N144A.

*Petioles*.—Length: About 18.4 cm. Diameter: Distally, about 4 mm and proximally, about 6 mm. Texture, upper and lower surfaces: Smooth, glabrous. Color, upper and lower surfaces: Close to 143A. Geniculum length: About 1.9 cm. Geniculum diameter: About 5 mm. Geniculum texture, upper and lower surfaces: Smooth, glabrous. Geniculum color, upper surface: Close to 144B; occasionally tinged with close to 152A to 152B. Geniculum color, lower surface: Close to 144C. Wing length: About 3.8 cm. Wing diameter: About 6 mm. Wing texture: Smooth, glabrous. Wing color: Close to 143B; towards the margins, close to 144C.

Inflorescence description:

*Inflorescence arrangement and flowering habit*.—Spathes with spadices; open inflorescences held above the foliar plane on strong scapes; flowering structures arise from leaf axils; freely and continuous flowering year-round in controlled temperature greenhouses in The Netherlands; typically about six developing and developed inflorescences per plant at one time; inflorescence development commences about 2.5 to 3.5 months after planting rooted young plants.

*Inflorescence longevity*.—On the plant, depending on temperature, spathes maintain good substance for about two months; inflorescences persistent.

*Fragrance*.—None detected.

*Spathes*.—Length: About 12.5 cm. Width: About 12 cm. Shape: Cordate; moderately concave. Apex: Mucronulate. Base: Cordate. Margin: Entire; occasionally slightly revolute. Aspect: About 45° to 80° from the scape axis. Texture, upper and lower surfaces: Smooth, glabrous; moderately coriaceous. Color: When developing, front surface: Close to 146D; towards the base, close to 144A; towards the apex, close to N45A; narrow marginal edges, close to N45A; midvein, close to N45A and lateral venation, close to 143A. When developing, rear surface: Close to 144A; towards the apex, close to 154C and at the apex, close to N45D; midvein, close to 46A and lateral venation, close to NN137B. Fully developed, front surface: Close to 144A; towards the apex, close to 150D and at the apex, close to N45C; narrow marginal edges, close to 46A; midvein, close to 46A and lateral venation, close to 146A; areas adjacent to the midvein, close to 46D, 47C and 47D; at the base of the spadix, close to N199A and N199B; with subsequent development, close to 150D and 154C. Fully developed, rear surface: Close to 144A; towards the apex, marbled with close to 150B and at the apex, close to 49A; narrow marginal edges, close to 185A; midvein, close to 185A and lateral venation, close to a blend of 143A and 146A; areas adjacent to the midvein, close to 49A; with subsequent development, close to 150D and 154C.

*Spadices*.—Length: About 5.9 cm. Diameter: About 1.1 cm. Shape: Cylindrical, slightly tapering towards the apex; apex, obtuse; base, obtuse; in cross-section, rounded. Aspect: About 0° to 20° from the scape axis. Color: Immature: Close to 42B; towards the apex, close to 34B. Mature: Close to a blend of 46A and 185A. Flowers: Type: Hermaphroditic. Quantity per spadix: About 200.Height: Less than 1 mm. Diameter: About 2.5 mm. Shape: Roughly square. Anther color: Close to 152C. Pollen amount: Scarce. Pollen color: Close to 155B. Stigma color: Close to 165B to 165C. Ovary color: Close to 75D; with subsequent development, becoming closer to 160B.

*Scapes*.—Length: About 35.2 cm. Diameter: About 5 mm. Strength: Strong, sturdy. Aspect: About 20° from vertical. Color: Close to a blend of 143A and 146A; distally, slightly to moderately tinged with close to 152A and 152B.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2297549' as herein illustrated and described.

* * * * *